United States Patent [19]

James et al.

[11] Patent Number: Plant 7,419

[45] Date of Patent: Jan. 15, 1991

[54] PECAN TREE NAMED 'JAMES EARLY' VARIETY

[75] Inventors: George W. James; George W. James, II, both of Brunswick, Mo.

[73] Assignee: James Pecan Farms, Inc., Brunswick, Mo.

[21] Appl. No.: 435,279

[22] Filed: Nov. 13, 1989

[51] Int. Cl.[5] ..... A01H 5/00

[52] U.S. Cl. ..... Plt./31

[58] Field of Search ..... Plt./31

*Primary Examiner*—James R. Feyrer

*Attorney, Agent, or Firm*—Burns, Doane, Swecker & Mathis

[57] ABSTRACT

A new and distinct variety of northern pecan tree (i.e., *Carya illinoensis*) is provided which can be distinguished from previously known pecan varieties by the extremely early maturity date of its pecan harvest. This permits the successful growing of a pecan crop at more northerly locations than has heretofore been possible, and facilities an earlier pecan harvest at existing pecan production regions of the north. The new variety forms on a regular basis quality kernels which release well from the shells. The tree exhibits a sturdy upright and spreading growth habit as well as excellent hardiness.

4 Drawing Sheets

SUMMARY OF THE INVENTION

The present new and distinct variety of pecan tree (i.e., *Carya illinoensis*) was discovered during the fall of 1984 as a mature seedling of unknown parentage while growing in a cultivated area. More specifically, the tree of the new variety was found while growing in a planting field on property operated by James Pecan Farms, Inc. and located in Chariton County, near Brunswick, Mo. The tree is estimated to have been approximately 10 to 15 years of age at the time of its discovery. Growing in nearby areas were various pecan trees including native northern pecan trees, trees of the James variety (U.S. Plant Pat. No. 1,361), and their progeny. The James variety presently is being marketed by the Stark Brothers Nurseries and Orchards Company of Louisiana, Mo., under the STARKING® Hardy Giant™ trademarks. Accordingly, even though the seed and pollen parents for the new variety are unknown, its parentage likely can be attributed to these trees.

Our attention was attracted to the original tree of the new variety primarily because of the extremely early maturity date of its nuts and the quality and abundance of the nuts which it produced. Native northern pecan tree of unidentified parentage in the area commonly require a killing frost before the husks being to open and yield nuts which ripen on approximately October 15th when grown in the area of Brunswick, Mo. Trees of the James variety (U.S. Plant Pat. No. 1,316) commonly yield nuts which ripen on approximately September 15th to 30th when grown in the area of Brunswick, Mo. The date of the first ripening of such nuts conveniently can be determined by observing the date when the husks around the nut begin to split (as illustrated). Once the husks of the pecans split, the pecan crop is of sufficient ripeness that the tree may be shaken by conventional means to cause the nuts to drop to the ground where they are harvested. Surprisingly, the new variety was found to form nuts which mature approximately 10 to 15 days before those of the James variety in the absence of a killing frost. The nuts of the new variety while grown at Brunswick, Mo., have been found to ripen very quickly during the last 10 days of August. During 1989, the husks of the nuts of the new variety, while grown at Brunswick, Mo., had undergone substantial splitting by September 1st, which date is about six weeks before the typical date for the first killing frost in the region. Such early ripening characteristic is of prime importance to the pecan grower since it requires a shorter growing season and permits the successful growing of a quality pecan crop at areas which are farther north provided a northern rootstock is selected. Since during 1989 pollination occurred on approximately May 15th and the husks of the nut had undergone substantial splitting by September 1st, a growing season of only approximately 109 days was required to produce a pecan crop. The new variety should permit the formation of mature pecans farther north than any previously known variety. Also, it permits the grower to place his annual harvest on the market at an earlier date than would otherwise be possible for major northern pecan growing areas, such as the Brunswick, Mo. area. The grower is thereby able to meet the demand for fresh pecans at a time when the nuts from conventional pecan plantings are not yet ready to harvest. The new variety additionally can serve as an attractive shade tree. Had we not discovered and preserved this new pecan variety it would have been lost to mankind.

The new variety additionally was observed to exhibit a sturdy upright and spreading growth habit as well as excellent hardiness since it has well withstood winter temperature as low as −20° F. without an adverse impact on the nut crop of the following harvest. The nut shells are thin and release easily from the kernels. The kernels are of high quality with good oil content.

Trees of the new variety have been asexually reproduced by both grafting and budding at Brunswick, Mo. The characteristics of the new variety are believed to be fully transmissible by such asexual propagation.

The new variety has been named the James Early variety.

BRIEF DESCRIPTION OF THE PHOTOGRAPHS

The photographs show various aspects of the new variety while grown at Chariton County, near Brunswick, Mo., wherein the color is illustrated as true as is reasonably possible in a depiction of this character.

Figure 1:
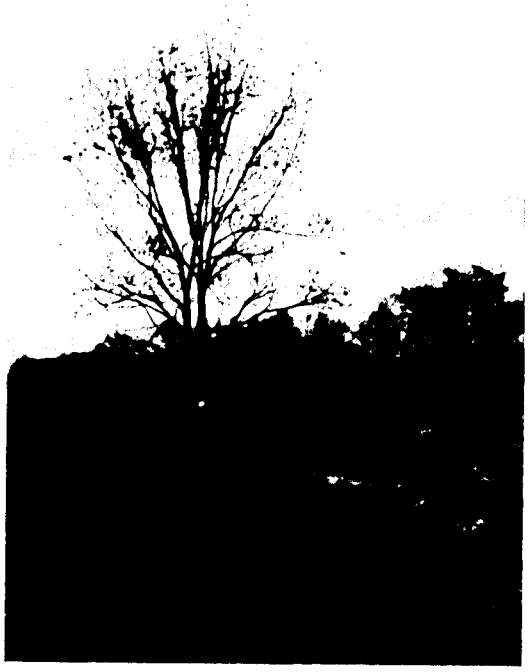
FIG. 1 shows the generally upright and spreading sturdy growth habit of the original tree of the new variety when observed during the winter.
Figure 2:
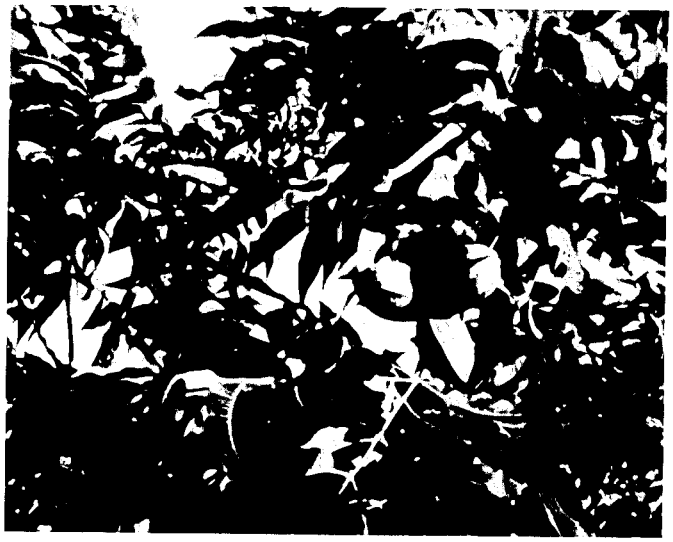
FIG. 2 shows typical foliage, and nuts of the new variety during early September wherein husk splitting around the nuts is apparent which is an indication of the extremely ripening characteristic of the new variety.
Figure 3:
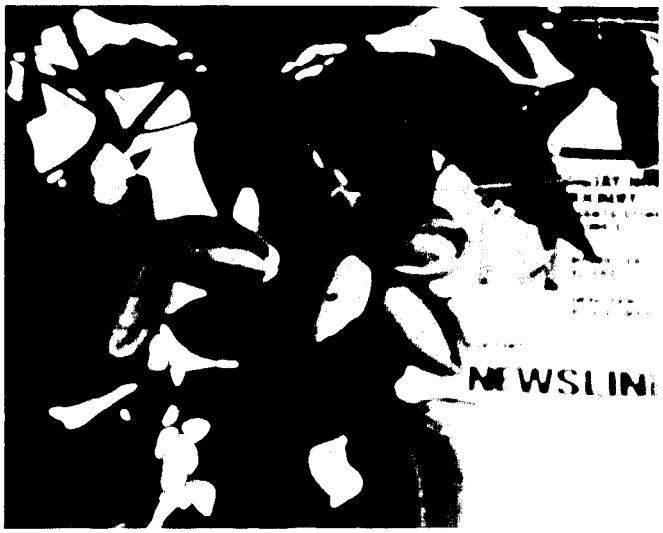

FIG. 3 illustrates for comparison purposes typical nuts of the new variety on the right and nuts on the James variety (U.S. Plant Pat. No. 1,361) on the left with the background being a September 1st newspaper wherein substantial husk opening is visible with respect to the new variety and no husk opening is visible for the comparative variety. One of the nuts of the comparative variety has been cut laterally so that an immature cross-section is visible and one of the nuts of the new variety has been removed from its husk.

Figure 4:
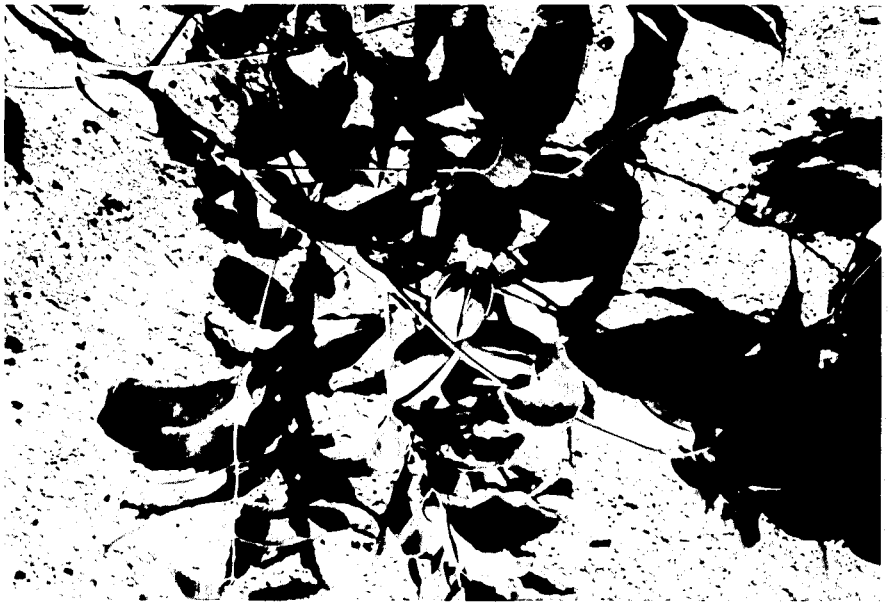

FIG. 4 illustrates typical foliage, branches, and nuts (with split husks) of the new variety following removal from the tree.

Figure 5:
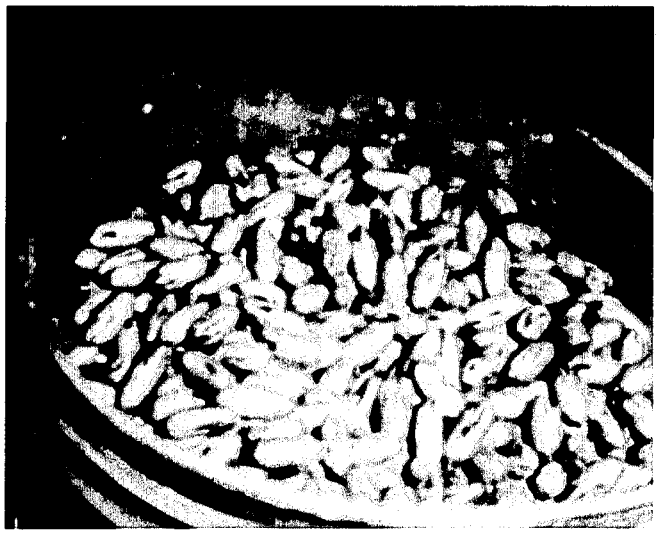

FIG. 5 illustrates a plurality of typical nuts of the new variety following removal from the husks.

Figure 6:
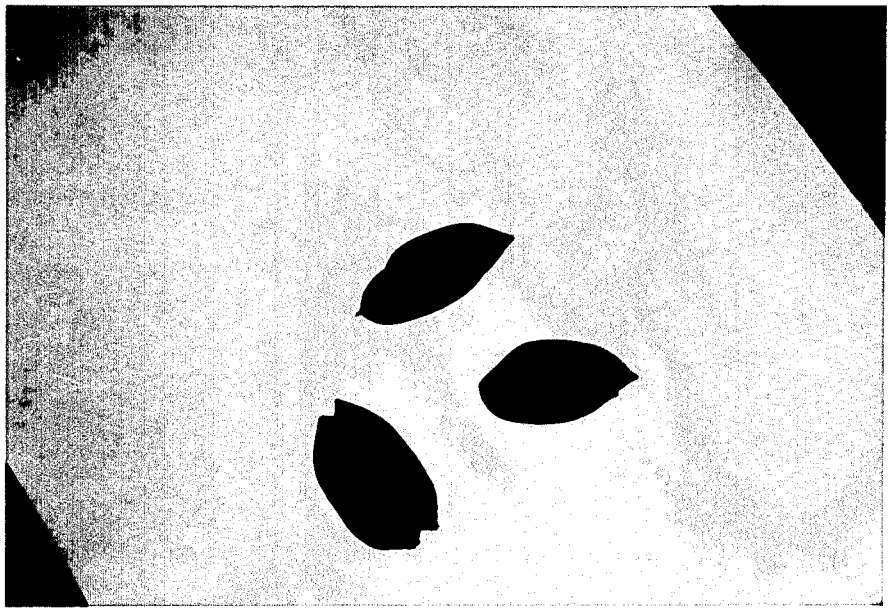

FIG. 6 illustrates in greater detail the typical configuration of the nuts of the new variety after they leave the husks wherein typical irregular black markings are visible on the outside of the shells primarily toward their sharp tips.

Figure 7:
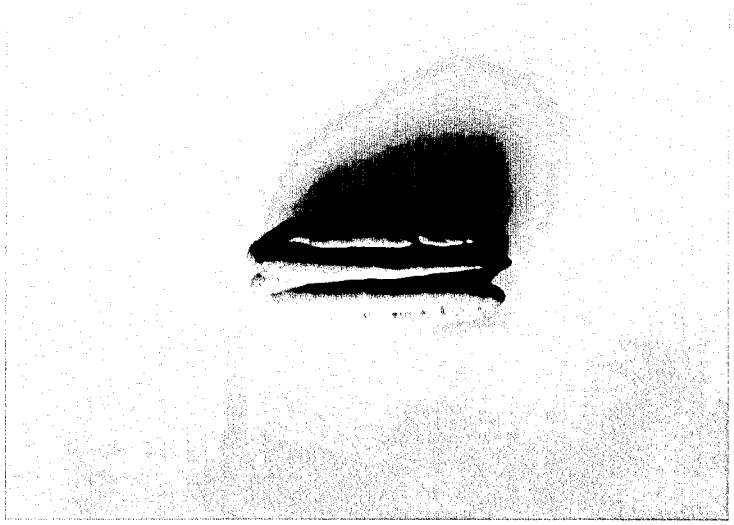

FIG. 7 illustrates with enlargement the configuration of a typical one-half kernel of the new variety after removal from the shell.

DETAILED DESCRIPTION

Unless otherwise indicated the characteristics of the new variety are believed to be substantially identical to those of the native northern pecan trees grown in Chariton County, near Brunswick, Mo., and elsewhere. The description of the new variety was made while grown at this same area.

The tree:

*Tree configuration.*—Medium size, vigorous, and sturdy with an upright and spreading growth habit (as illustrated).

*Productivity.*—Good regular bearer of quality nuts.

*Foliage.*—Abundant and large. The leaflets commonly are of irregular size and commonly range in length from approximately 3 to 6 inches and in width from approximately ¾ to 2 inches. The same general coloration as that of the native northern pecan trees is observed.

*Buds.*—Round and relatively blunt in configuration.

*Catkins.*—Small in size. Appear in May at approximately the same time as the native northern pecan trees.

*Hardiness.*—Excellent. Has withstood −20° F. during the winter with no deleterious results. Accordingly, there is less danger of losing a crop because of cold weather.

*Resistance to insects and disease.*—A relative lack of damage by insects and disease has been observed.

The nuts:

*Ripening.*—Even and extremely early. A typical harvest time is September 1st to September 5th. No killing frost is required to activate husk splitting and harvest.

*Quantity.*—Abundant.

*Maturity.*—Extremely early since requires a shorter growing season. Approximately 10 to 15 days earlier than the James variety which is marketed by Stark Brothers Nurseries and Orchards Company of Louisiana, Mo., under the STARKING® Hardy Giant™ trademarks (U.S. Plant Pat. No. 1,361).

*Tenacity.*—Free.

*Cluster size.*—Commonly 3 to 5 medium-sized nuts per cluster.

*Configuration.*—Sharply pointed tip. Commonly measure approximately 1½ inches in length and approximately ⅝ inch in diameter at the widest area.

*Weight.*—Approximately 104 nuts will weight one pound.

*Shell.*—Thin, slender, cracks easily and releases kernel well. Typical wood brown coloration with heavy black markings located mostly toward the sharply pointed tip (as illustrated).

*Kernel.*—High quality, flavor is excellent, light in coloration, high in oil content, the halves are thick and oblong in shape with a short point, texture is firm, easily retrieved in whole halves, and the sutures are open and even.

We claim:

1. A new and distinct variety of pecan tree having a sturdy upright and spreading growth habit and excellent hardiness which bears in abundance quality nuts which mature 10 to 15 days earlier than the James variety (U.S. Plant Pat. No. 1,361), substantially as illustrated and described.

* * * * *